United States Patent
Hocken et al.

(10) Patent No.: US 9,638,127 B2
(45) Date of Patent: May 2, 2017

(54) METHOD OF VERIFYING PARTICULATE MATTER SENSOR VALIDITY

(71) Applicant: DELPHI TECHNOLOGIES, INC., Troy, MI (US)

(72) Inventors: Lary R. Hocken, Davison, MI (US); Robert J. A. Van Der Poel, Schweich (LU)

(73) Assignee: Delphi Technologies, Inc., Troy, MI (US)

( * ) Notice: Subject to any disclaimer, the term of this patent is extended or adjusted under 35 U.S.C. 154(b) by 159 days.

(21) Appl. No.: 14/165,843

(22) Filed: Jan. 28, 2014

(65) Prior Publication Data

US 2015/0211429 A1 Jul. 30, 2015

(51) Int. Cl.
| | |
|---|---|
| *G01R 27/08* | (2006.01) |
| *G01N 27/00* | (2006.01) |
| *F02D 41/22* | (2006.01) |
| *G01R 35/00* | (2006.01) |
| *G01N 15/06* | (2006.01) |
| *F02D 41/02* | (2006.01) |
| *F02D 41/14* | (2006.01) |
| *G01M 15/10* | (2006.01) |
| *G01N 15/00* | (2006.01) |

(52) U.S. Cl.
CPC ......... *F02D 41/222* (2013.01); *F02D 41/029* (2013.01); *F02D 41/1466* (2013.01); *G01N 15/0606* (2013.01); *G01N 15/0656* (2013.01); *G01R 35/005* (2013.01); *F02D 41/1494* (2013.01); *F02D 2200/0812* (2013.01); *G01M 15/102* (2013.01); *G01N 2015/0046* (2013.01)

(58) Field of Classification Search
CPC .. F02D 41/222; F02D 41/1466; F02D 41/029; F02D 41/1494; F02D 2200/0812; G01N 15/0606; G01N 15/0656; G01N 2015/0046; G01R 35/005; G01M 15/102
USPC ................................ 324/601, 705; 73/28.01
See application file for complete search history.

(56) References Cited

U.S. PATENT DOCUMENTS

| | | | |
|---|---|---|---|
| 4,656,832 A | 4/1987 | Yukihisa et al. | |
| 6,634,210 B1 | 10/2003 | Bosch et al. | |
| 7,157,919 B1 * | 1/2007 | Walton ................... | F01N 9/002 |
| | | | 324/639 |
| 7,954,230 B2 | 6/2011 | Nelson | |
| 8,095,294 B1 * | 1/2012 | Griffiths et al. ............. | 701/103 |
| 2008/0282769 A1 | 11/2008 | Nelson | |

(Continued)

*Primary Examiner* — Farhana Hoque
(74) *Attorney, Agent, or Firm* — Joshua M. Haines

(57) ABSTRACT

A method for verifying the validity of an output of a particulate matter sensor mounted in an engine exhaust system downstream of a diesel particulate filter, the particulate matter sensor including a pair of electrodes spaced apart from each other, includes initiating regeneration of the diesel particulate filter, applying and maintaining a higher than nominal voltage across the electrodes following the step of initiating regeneration of the diesel particulate filter, and measuring an electrical parameter across the electrodes while the higher voltage is applied across the electrodes, where the electrical parameter is indicative of an amount of soot accumulated on the sensor. The reading of accumulated soot is evaluated to determine whether the sensor is indicating that the amount of accumulated soot is within an expected range based on a clean diesel particulate filter and the elevated applied voltage.

9 Claims, 4 Drawing Sheets

(56) References Cited

U.S. PATENT DOCUMENTS

| | | |
|---|---|---|
| 2008/0283398 A1 | 11/2008 | Nelson et al. |
| 2010/0180668 A1* | 7/2010 | Kruse et al. ................. 73/28.01 |
| 2012/0119759 A1 | 5/2012 | Nelson et al. |
| 2012/0255340 A1* | 10/2012 | Ante et al. ................... 73/23.31 |
| 2013/0002271 A1* | 1/2013 | Hocken ............... F02D 41/1466 |
| | | 324/705 |

* cited by examiner

METHOD OF VERIFYING PARTICULATE MATTER SENSOR VALIDITY

BACKGROUND OF THE INVENTION

This invention relates generally to sensors for detecting electrically conductive particulate matter, such as soot, and more particularly to a method and system for diagnosing potential failure modes in such sensors.

Incomplete combustion of certain heavy hydrocarbon compounds, such as heavy oils, diesel fuel, and the like may lead to particulate formation (e.g., soot). In the operation of internal combustion engines, excessive particulate formation can lead to "smoking" of the engine, which causes air pollution even though the carbon monoxide, hydrocarbons, and other pollutant components of the gaseous state exhaust emissions may be relatively low. Emission regulations require many engines to limit the levels of particulate emissions, and various control technologies such as diesel particulate filters (DPF) have been employed for this purpose.

In order to monitor the emission of particulate matter in the exhaust streams of certain types of internal combustion engines, e.g., to assess the effectiveness of DPF's, it is known to provide a particulate sensor system for detecting the level of particulate concentration emitted from an exhaust gas. Various particulate sensors have been proposed, including those shown in U.S. Pat. No. 4,656,832 issued to Yukihisa et al., U.S. Pat. No. 6,634,210 issued to Bosch et al., U.S. Pat. No. 7,954,230 issued to Nelson et al., U.S. Pat. Publ. No. 2008/0283398 A1, U.S. Pat. Publ. No. 2008/0282769 A1, U.S. Patent Application Publication No. 2012/0119759 A1, and U.S. Patent Application Publication No. 2013/0002271 A1, the disclosures of each of which are hereby incorporated by reference in their entirety.

Particulate sensors such as those described above generally have a pair of spaced apart sensing electrodes disposed on a substrate. The sensing electrodes are coupled to a measurement circuit by way of electrically conductive leads. The operating principle of the particulate sensor is based on the conductivity of the particulates (e.g., soot) deposited between the sensing electrodes. The electrical resistance between the sensing electrodes is relatively high when the sensor is clean but such resistance decreases as soot particulates accumulate. These sensors also have a heater that can be selectively activated to burn off the soot particulates to "reset" the sensor to a known, base "clean" state.

Regulatory agencies may require that a particulate sensor system has self-diagnostic capability to identify a failure of the particulate sensor to perform its primary function of measuring soot. However, for diagnostic purposes, it can be difficult to distinguish between various states that may occur during various engine operating conditions, such as between: (i) a faulty state such as when the sensor is "poisoned" by a non-conductive or semi-conductive contaminant deposited on the electrodes preventing soot from contacting the electrodes, which presents as a very high resistance between the sensing electrodes, and (ii) a normal state, such as when a sensor has just been cleaned and the DPF is working properly (i.e. preventing soot from passing through to the sensor), which also presents as a very high resistance.

Accordingly, there is a need for particulate sensor diagnostics that can accurately verify particulate sensor operation with a properly operating DPF.

BRIEF SUMMARY OF THE INVENTION

In a first aspect of the invention, a method for verifying the proper operation of a particulate matter sensor is presented. The method comprises applying an elevated voltage to the sensor after regeneration of a diesel particulate filter in an engine exhaust stream located upstream of the sensor has commenced, monitoring the indicated resistance across the sensing electrodes of the sensor with the elevated voltage applied, and evaluating the behavior of the indicated resistance across the sensing electrodes to determine if the behavior is consistent with the behavior that would be expected from a properly-operating sensor. After a period of time, the voltage applied to sensor is reduced to a nominal voltage, the nominal voltage being of a lower magnitude than the elevated voltage.

In a further aspect of the invention, control of the engine is perturbed so as to increase soot emissions from the engine for a short period of time while the sensor is being operated at the elevated voltage level. The soot accumulation determined by the sensor is compared to a predetermined estimate of soot rate downstream of a properly operating diesel particulate filter under these special engine conditions to verify that the sensor is able to measure the soot.

DETAILED DESCRIPTION OF THE INVENTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "left", "right", "horizontal", "vertical", "bottom", and "top" are used herein, unless otherwise noted, merely for convenience of description, and are not limited to any one position or spatial orientation. Finally, unless defined otherwise, technical and scientific terms used herein have the same meaning as is commonly understood by one of skill in the art to which this invention belongs.

Figure 1:
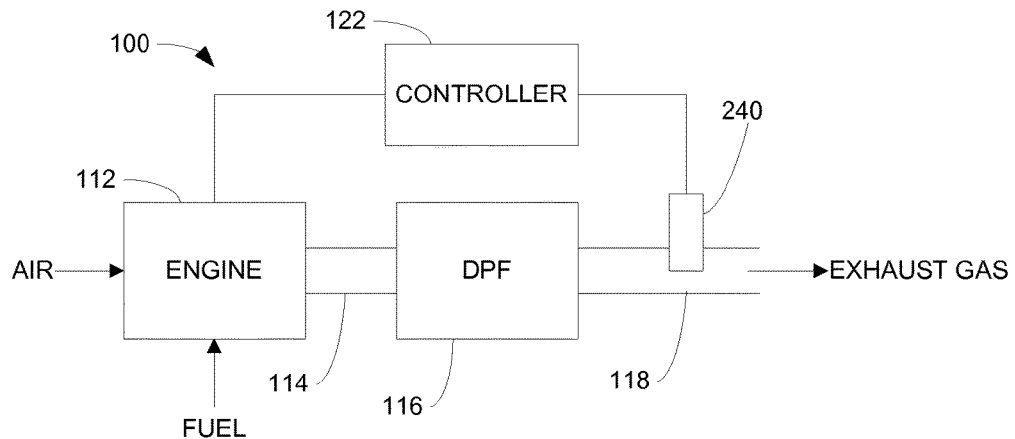
FIG. 1 is a simplified schematic diagram showing a particulate control system in an engine exhaust system.

As described above, diesel particulate filter (DPF) is commonly used to prevent soot from exiting the tailpipe of an exhaust system used with an internal combustion engine. A simplified schematic diagram of a particulate control system in an engine exhaust system is presented in FIG. 1. Air and fuel enter an engine 112, where combustion of an air/fuel mixture takes place. Combustion byproducts from the engine 112 are exhausted through a first exhaust pipe 114 to a DPF 116. After passing through the DPF, the exhaust gas passes through a second exhaust pipe 118 to be exhausted to atmosphere. A particulate matter (PM) sensor 240 is located so as to be exposed to the exhaust gas downstream of the DPF 116. The PM sensor 240 is used to detect if the exhaust gas in the second exhaust pipe 118 includes an amount of soot that would be indicative of a failure, such as a crack, of the DPF 116. A controller 122 is also depicted in FIG. 1 with an interface to the PM sensor 240. The controller 122 measures the resistance across the electrodes of the PM sensor 240 and controls the heater used to periodically clean soot from the PM sensor 240. While shown as a single controller 122 that also interfaces with the engine 112, it will be appreciated that the functions related to engine control and the functions related to PM sensor interface may be partitioned differently, e.g. using a plurality of controllers including one or more separate controllers dedicated to control and measurement functions associated with the PM sensor 240 and communicating with an engine controller 122.

The DPF 116 typically includes a porous element through which exhaust gas is passed. Pore size is selected so as to trap soot particles in the DPF 116. As soot accumulates in the DPF 116, the pores become clogged and flow restriction (backpressure) through the DPF increases. The DPF 116 must periodically be cleaned to remove accumulated soot particles. This cleaning process, known as regeneration, typically involves controlling the engine so as to increase the temperature of the exhaust gas through the DPF 116 to cause combustion of the soot that has accumulated in the DPF.

As described above, a PM sensor 240 is used in an exhaust system to diagnose a failed DPF 116. The basic technology utilizes a resistance based device that has parallel electrodes where particulate matter or soot accumulates in a gap in between the electrodes. Since the soot is conductive, as it accumulates the measured resistance of the sensor will decrease with increasing soot content.

Three main effects contribute to the accumulation of soot on the sensor. These are electrophoretic, thermophoretic, and direct impact of soot on the sensor. The electrophoretic effect is due to applied voltage across the electrodes which attract the charged soot particles. As this applied voltage increases attraction of soot will also increase. The thermophoretic effect describes the response of soot to a thermal gradient, with a tendency for increased accumulation of soot when the sensor temperature is lower than the soot temperature. Direct impact is a mechanical accumulation such that the soot is adhered to the sensor when it impinges on the sensor.

It has been observed that as a DPF 116 accumulates soot the filtering efficiency of the DPF 116 (i.e. the ability of the DPF 116 to prevent soot from passing through) increases. Without being bound to a theory, it is believed that this is due to accumulated soot in the DPF 116 lowering the effective pore size of the porous element in the DPF 116. Conversely, it has been observed that a DPF 116 is less efficient (i.e. the DPF 116 allows more soot to pass through) just after regeneration of the DPF 116 occurs because the effective pore size is larger when the DPF 116 is clean.

Figure 2:
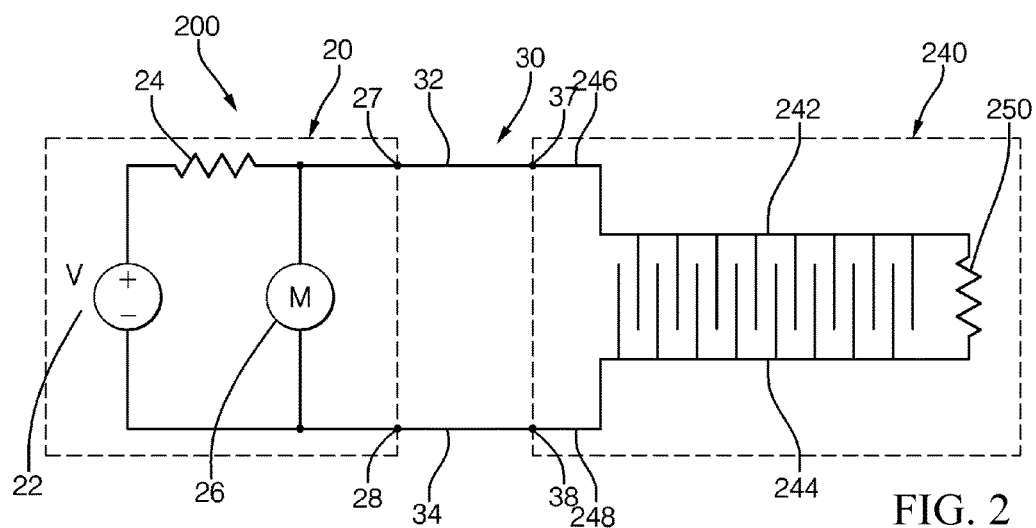
FIG. 2 is an electrical schematic of a particulate matter sensing system.

FIG. 2 is an electrical schematic of a particulate matter sensing system 200. The system 200 may be generally considered as partitioned as indicated into a controller portion 20, a wiring harness portion 30, and a sensing element portion 240. The system may also include means for controlling a heater disposed on the sensing element to allow cleaning of the sensing element, not shown in FIG. 2. The function performed by the controller portion 20 of FIG. 2 may be embodied in a separate controller or may be included in the controller 122 depicted in FIG. 1.

The controller portion 20 comprises a means for measuring the impedance of a circuit connected thereto. In the exemplary controller portion 20 in FIG. 2, the impedance measurement means includes a voltage source 22 that provides a voltage value $V_{supply}$, a pull-up resistor 24 having a resistance value $R_{pullup}$, and a voltage measurement means 26. While voltage source 22 is depicted in FIG. 2 as a DC source with a given polarity, it will be appreciated that voltage source 22 can alternatively be an AC source, a DC source having opposite polarity from what is depicted, or a source providing both an AC and a DC voltage component, without departing from the inventive concept described herein. The controller portion 20 electrically interfaces to the wiring harness portion 30 by connection means 27 and 28. The wiring harness portion 30 includes conductors 32 and 34. The wiring harness portion 30 electrically interfaces to the sensing element portion 240 by connection means 37 and 38. The sensing element portion 240 includes a first electrode 242 electrically connected by conductor 246 to connection means 37, and a second electrode 244 electrically connected by conductor 248 to connection means 38.

The sensing element portion 240 in FIG. 2 contains an additional bias resistor 250 having a resistance value of $R_{bias}$ electrically connected between conductors 246 and 248. The resistance of the sensing element $R_{sensor}$ as measured between connection means 37 and connection means 38 is the parallel combination of $R_{bias}$ and $R_{particulate}$, the resistance resulting from particulate matter bridging the gap between the first electrode 242 and the second electrode 244. $R_{sensor}$ can be represented mathematically as:

$$R_{sensor} = \frac{R_{bias} \times R_{particulate}}{R_{bias} + R_{particulate}}$$

In the absence of particulate matter on sensing element 240, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 242 and the second electrode 244, the effective sensor resistance $R_{sensor}$ will decrease from its maximum value of $R_{bias}$.

For the particulate matter sensing system 200 depicted in FIG. 2, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

One of the major challenges with resistive PM sensor technology is the ability to prove that the sensor is working properly when the DPF 116 is still good, as there is essentially no soot coming down the exhaust pipe 118 downstream of the DPF. A sensor may exhibit a failure mode (e.g. electrically non-conductive contamination, internal open circuit) that results in a resistance reading that is indistinguishable from a properly operating sensor in the absence of soot. In an aspect of the present invention, readings from the PM sensor 240 are evaluated at times when soot levels in the exhaust pipe 118 are likely to be elevated, for example when the DPF 116 has just been cleaned.

The voltage imposed across the sensing electrodes of a PM sensor 240 depends on the voltage $V_{supply}$ provided by the voltage source 22, which is typically selected to be 5 volts. Initial testing has shown that soot is not easily measurable using a typical sensor reference voltage (i.e. 5 volts), even after a DPF cleaning event when the filtering efficiency of the DPF is at its lowest.

One way to improve the ability to measure soot is to increase the applied voltage across the electrodes, thus increasing the electrophoretic effect. This would require a controller that has the ability to change the voltage applied across the sensor element during operation. To evaluate this approach, testing was performed on a population of soot sensors mounted in a gas stream that contained a controlled concentration of soot. For each sensor, a response time was determined, where the response time is defined as the elapsed time from the end of a sensor cleaning event until the total sensor resistance $R_{sensor}$ (i.e. the parallel combination of $R_{bias}$ and $R_{particulate}$) decreased to a specific percentage of the bias resistance $R_{bias}$. Testing was repeated using a number of different values of $V_{supply}$. Results of this testing are shown in Table 1 below, and are presented graphically in FIG. 3.

TABLE 1

| Supply Voltage (volts) | Average Total Response Time (seconds) |
|---|---|
| 5 | 899.5 |
| 10 | 341.6 |
| 12 | 264.8 |
| 14 | 213.5 |
| 16 | 177.1 |
| 20 | 129.7 |
| 24 | 100.5 |

Figure 3:
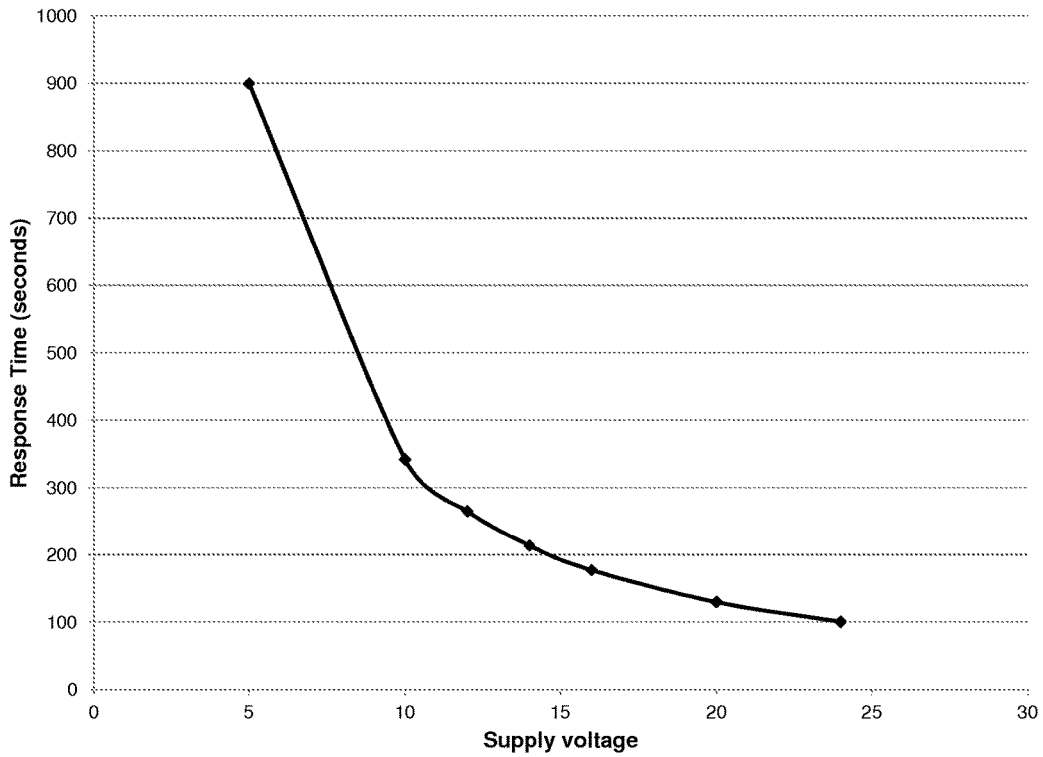
FIG. 3 is a chart showing the dependence of particulate sensor response time on applied voltage across the electrodes of the particulate sensor.

The results presented in Table 1 and in FIG. 3 illustrate the electrophoretic effect on a PM sensor. While each sensor was exposed to the same soot concentration in a gas stream, increasing the supply voltage resulted in more of the soot in the gas stream adhering to the sensor with a resultant decrease in the amount of time required to capture sufficient soot to reduce the sensor resistance to the same predetermined percentage of the bias resistance used in the response time definition. This effect is used in an aspect of the present invention by operating the sensor at a voltage of higher magnitude than the nominal operating voltage for a period of time, to enhance the ability of a diagnostic system to capture sufficient soot to verify proper operation of the sensor in a low soot environment such as would be present with a properly functioning DPF.

Figure 4:
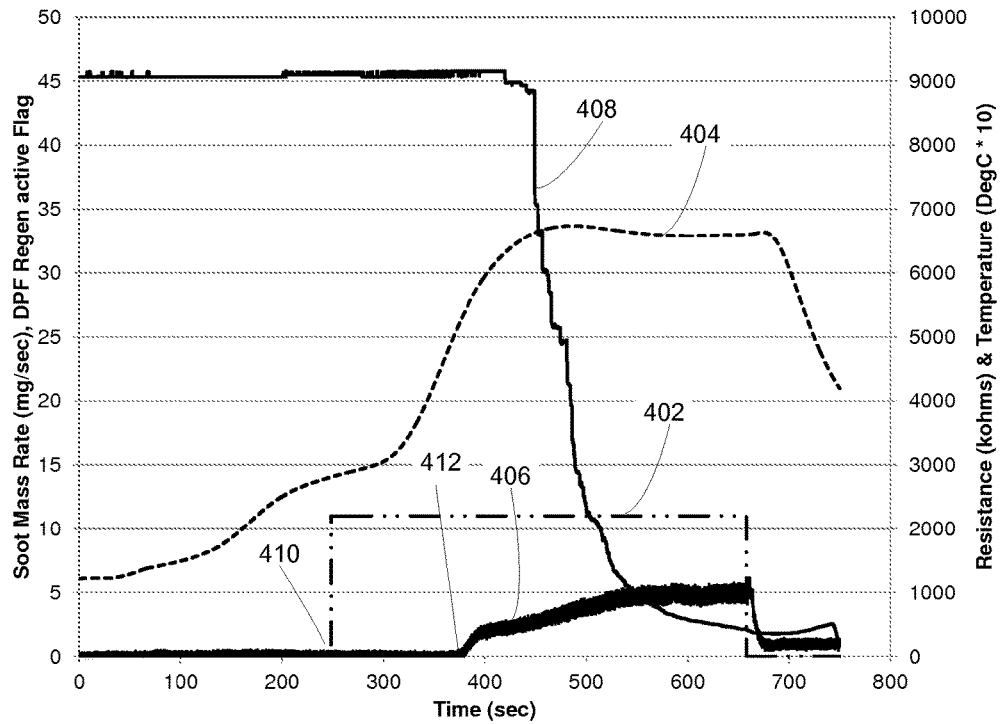
FIG. 4 is a chart showing a soot mass rate downstream of a diesel particulate filter in a time interval around the regeneration time of the diesel particulate filter.

FIG. 4 is a chart showing a soot mass rate downstream of a diesel particulate filter in a time interval around the regeneration time of the diesel particulate filter. Trace 402 is a logic trace that has a high level when a DPF regeneration event is commanded and a low level otherwise. When a DPF regeneration event is commanded, a controller adjusts engine operating conditions so as to raise the temperature of the exhaust from the engine to a level sufficient to cause spontaneous combustion (also known as auto-regeneration) of soot that has accumulated in the DPF 116. Trace 404 represents an exhaust temperature, which can be seen to rise and fall in response to the DPF regeneration flag shown in trace 402. Trace 406 is the output of an independent instrument disposed to measure the actual soot mass rate in the exhaust pipe 118. Trace 408 represents the output resistance of a PM sensor 240 disposed in the exhaust pipe 118, with a supply voltage of 12 volts applied to the PM sensor 240. It is to be understood that the 12 volt level used in this demonstration is an example of an elevated voltage level and is not to be construed to limit practice of the invention to any particular voltage level.

With continued reference to FIG. 4, a DPF regeneration event is commanded at the time indicated as 410. During the time interval immediately following time 410, the exhaust temperature 404 increases and soot in the DPF 116 is combusted. At the time indicated as 412, sufficient soot in the pores of the DPF 116 has burned to reduce the filtering efficiency of the DPF 116 such that soot is detectable downstream of the DPF, as shown by the trace 406 representing the output of a soot sensing instrument. As shown by the decrease in the resistance across the PM sensor 240 as shown in trace 408, with a supply voltage of 12 volts the PM sensor 240 is also able to respond to low levels of soot passing through a normally operating DPF 116 after regeneration of the DPF 116.

While operating a PM sensor 240 at an elevated voltage (e.g. 12 volts) improves the ability to recognize low levels of soot, which allows proper operation of the PM sensor 240 to be verified in the absence of a DPF fault, the timing of this voltage shift after the DPF regeneration event is also critical as the higher voltage may also attract contamination, which is undesirable. As used herein, contamination refers to electrically nonconductive material that may be present in the combustion byproducts in the exhaust stream, where said nonconductive material would degrade the functionality of the PM sensor if deposited on the PM sensor. The post-DPF regeneration increase in soot concentration has been seen for a limited time after the DPF regeneration is complete. The higher voltage would only need to be applied for a short duration at which the sensor validity has been proven. The sensor may then be cleaned to prove that the measured resistance was due to removable material (i.e. soot) on the sensing element. Then the applied voltage to the PM sensor 240 would be returned to a lower value (e.g. 5 volts) or turned off until an appropriate time to minimize the possibility of attracting contamination.

During or after a DPF regeneration event if soot concentration is insufficient some additional measures could be demanded to increase soot emissions for a short time, such as increasing EGR rate or reducing injection rail pressure. A specific soot emission model which estimates soot mass behind a proper DPF during these special conditions could be compared to the sensor soot mass. Another option is to use the sensor accumulation time to calculate accumulated soot mass and compare this to a limit soot mass to determine whether the sensor is working correctly.

Figure 5:
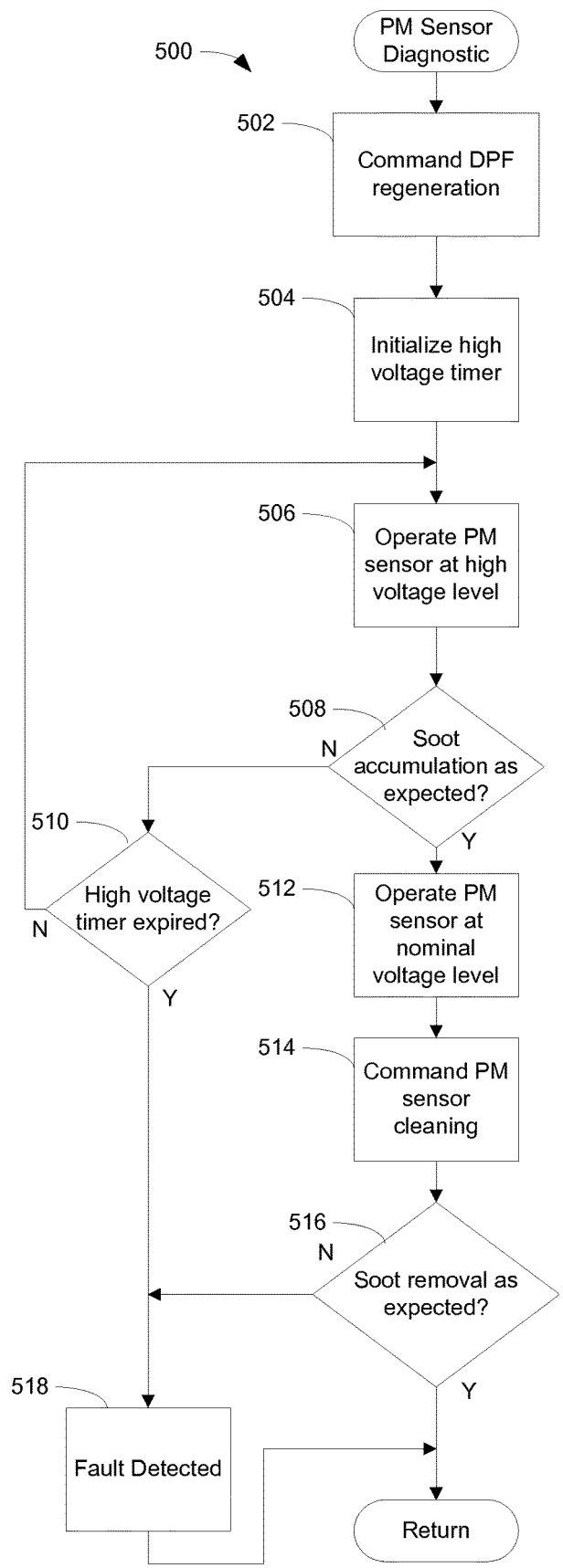
FIG. 5 is a flowchart depicting elements of a first embodiment of the present invention.

FIG. 5 is a flowchart of a non-limiting embodiment of a diagnostic method 500 that incorporates aspects discussed above. In step 502, a DPF regeneration event is initiated so as to take advantage of the reduction of filtering efficiency exhibited by a clean DPF. In step 504 a timer is initialized. As shown in step 506, the PM sensor is operated at a high voltage relative to the nominal operating voltage of the PM sensor. In step 508, the amount of soot accumulation indicated by the PM sensor is evaluated to determine if the PM sensor is recognizing a soot level that is expected for the present conditions of clean DPF and high PM sensor voltage. If the determination in step 508 is that indicated soot accumulation is less than expected, the method passes to step 510 where the timer is checked. If the timer has not expired, the method returns to step 506.

If the determination in step 508 is that the indication of soot accumulation is as expected, that is to say that the PM sensor is capable of recognizing soot, the method passes to step 512. In step 512 the operating voltage of the PM sensor is reduced to a nominal voltage level. In this way, the PM sensor is less likely to attract undesirable contamination that may impair its performance. In step 514, cleaning of the PM sensor is commanded. In step 516, the PM sensor output is evaluated, perhaps after a time delay, to determine whether the PM sensor indicates expected soot removal performance.

Returning to step 510, if the timer has expired without an indication in step 508 that soot accumulation is as expected, this condition may be indicative of a PM sensor fault, and the method proceeds to step 518. Likewise, if the determination in step 516 is that the PM sensor did not indicate soot removal as expected from a sensor cleaning event in step 514, this condition may also be indicative of a PM sensor fault, and the method proceeds to step 518.

Upon reaching step 518 as a result of detection of a fault, a course of action may be selected from several possibilities. For example, a flag may be set in a controller and/or an indicator lamp may be illuminated. Alternatively, a more aggressive PM sensor diagnostic routine may be initiated. A non-limiting example of a more aggressive diagnostic routine is presented in FIG. 6.

Figure 6:
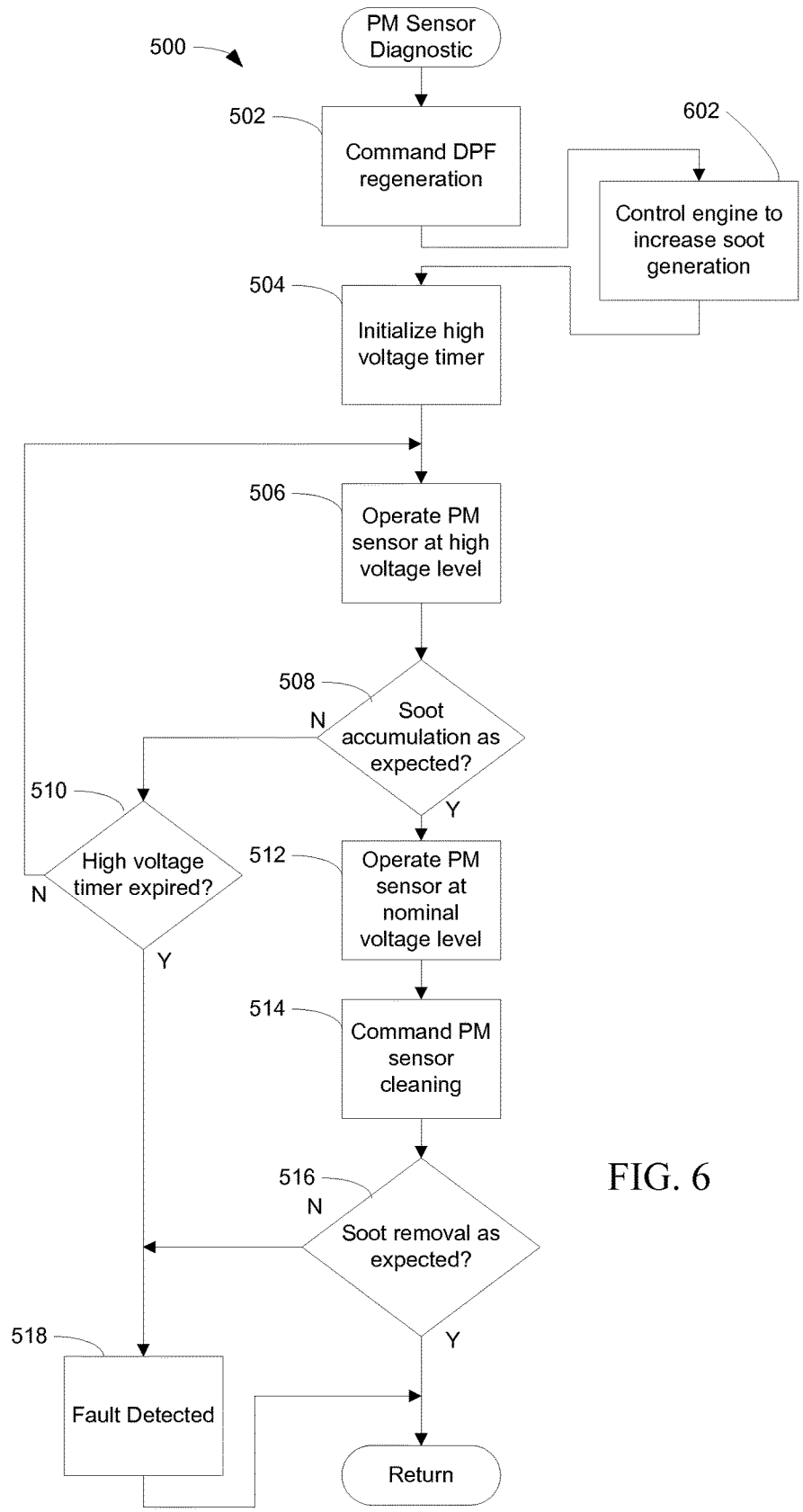
FIG. 6 is a flowchart depicting elements of a second embodiment of the present invention.

The PM sensor diagnostic method depicted in the flowchart of FIG. 6 is similar to the PM sensor diagnostic method in FIG. 5, and steps having the same function use the same numbering as in FIG. 5. The method depicted in the flowchart of FIG. 6 includes an additional step 602. In step 602, the engine is controlled so as to increase the soot generation from the engine while the PM sensor evaluation is taking place as described in the discussion of FIG. 5. Step 602 may include any known method of increasing engine soot generation, including but not limited to controlling EGR or controlling fuel rail pressure.

It may be desirable to follow the method depicted in FIG. 6 in lieu of the method depicted in FIG. 5. Alternatively, it may be desirable to follow the method depicted in FIG. 5 initially, and only employ the method of FIG. 6 if the determination in step 518 of FIG. 5 is that the PM sensor has not detected the expected soot accumulation in step 508. In such a way, the likelihood is reduced of falsely indicating a PM sensor fault when in reality insufficient soot was available for the PM sensor to detect.

While this invention has been described in terms of embodiments thereof, it is not intended to be so limited, but rather only to the extent set forth in the claims that follow.

The invention claimed is:

1. A method for verifying the validity of an output of a particulate matter sensor mounted in an engine exhaust system downstream of a diesel particulate filter, the particulate matter sensor comprising a pair of electrodes spaced apart from each other, the method comprising the steps of:
 initiating regeneration of the diesel particulate filter;
 applying and maintaining a first voltage across the electrodes following the step of initiating regeneration of the diesel particulate filter;
 measuring an electrical parameter across the electrodes while the first voltage is applied across the electrodes, the electrical parameter being indicative of an amount of soot accumulated on the sensor;
 evaluating the electrical parameter to determine whether the sensor is indicating that the amount of accumulated soot is within a first predetermined range;
 determining that the sensor is operating properly if the electrical parameter is indicating that the amount of accumulated soot is within the first predetermined range.

2. The method of claim 1 further including the step of indicating that the sensor is not operating properly if the electrical parameter is not within the first predetermined range within a predetermined time interval after the first voltage is first applied across the electrodes.

3. The method of claim 1 further including the step of reducing the voltage applied across the electrodes from the first voltage to a second voltage, the second voltage being of lower magnitude than the first voltage.

4. The method of claim 3 wherein the voltage is reduced from the first level to the second level after the step of determining that the sensor is operating properly.

5. The method of claim 1 wherein, if the electrical parameter is indicating that the amount of accumulated soot is within the first predetermined range the method further includes the steps of:
 commanding a sensor cleaning event;
 measuring the electrical parameter after commanding the sensor cleaning event;
 evaluating the electrical parameter to determine whether the sensor is indicating that the accumulated soot is being successfully cleaned from the sensor; and
 indicating that the sensor is not operating properly if the sensor is not indicating that the accumulated soot is being successfully cleaned from the sensor.

6. The method of claim 1 further comprising controlling the engine so as to increase an amount of soot generated by the engine while the first voltage is applied and maintained across the electrodes.

7. The method of claim 6 wherein the step of controlling the engine comprises controlling exhaust gas recirculation to the engine.

8. The method of claim 6 wherein the step of controlling the engine comprises controlling engine fuel rail pressure.

9. An apparatus comprising:
 a processor, and
 a memory storing instructions that, when executed, cause the apparatus to:
 initiate regeneration of the diesel particulate filter;
 apply and maintain a first voltage across the electrodes following the step of initiating regeneration of the diesel particulate filter;
 measure an electrical parameter across the electrodes while the first voltage is applied across the electrodes, the electrical parameter being indicative of an amount of soot accumulated on the sensor;
 evaluate the electrical parameter to determine whether the sensor is indicating that the amount of accumulated soot is within a first predetermined range; and
 determine that the sensor is operating properly if the electrical parameter is indicating that the amount of accumulated soot is within the first predetermined range.

* * * * *